United States Patent
Pirolli et al.

(10) Patent No.: US 10,605,068 B2
(45) Date of Patent: Mar. 31, 2020

(54) DOWNHOLE ELECTROCHEMICAL FLUID SENSOR AND METHOD OF USING SAME

(71) Applicant: Schlumberger Technology Corporation, Sugar Land, TX (US)

(72) Inventors: Laurent Pirolli, Stafford, TX (US); Gary Martin Oddie, Cambridgeshire (GB); Andrew Meredith, Cambridge (GB); Nathan S. Lawrence, Cambridgeshire (GB); Kay McGuinness, Cambridgeshire (GB); John Collins, Herts (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/109,786

(22) Filed: Dec. 17, 2013

(65) Prior Publication Data

US 2015/0167445 A1   Jun. 18, 2015

(51) Int. Cl.
*E21B 47/00* (2012.01)
*G01N 27/404* (2006.01)
*G01N 33/00* (2006.01)

(52) U.S. Cl.
CPC ......... *E21B 47/00* (2013.01); *G01N 27/4045* (2013.01); *G01N 33/0044* (2013.01); *Y10T 436/184* (2015.01)

(58) Field of Classification Search
None
See application file for complete search history.

(56) References Cited

U.S. PATENT DOCUMENTS

| | | |
|---|---|---|
| 6,223,822 B1 | 5/2001 | Jones |
| 6,939,717 B2 | 9/2005 | Jiang et al. |
| 7,025,138 B2 | 4/2006 | Kurkjian et al. |
| 7,222,671 B2 | 5/2007 | Caudwell et al. |
| 7,458,252 B2 | 12/2008 | Freemark et al. |
| 7,520,160 B1 | 4/2009 | Toribio et al. |
| 8,177,958 B2 | 5/2012 | Lawrence et al. |
| 2003/0134426 A1* | 7/2003 | Jiang ............... E21B 47/011 436/121 |
| 2003/0159930 A1* | 8/2003 | Kiesele ............. G01N 27/4045 204/415 |

(Continued)

OTHER PUBLICATIONS

Lawrence et al. (Sensors and Actuators B, 69, 2000, 189-192).*

(Continued)

*Primary Examiner* — Gurpreet Kaur
*Assistant Examiner* — Steven E Rosenwald

(57) ABSTRACT

An electrochemical fluid sensor for a downhole production tool positionable in a wellbore penetrating a subterranean is provided. The wellbore has a downhole fluid therein. The electrochemical fluid sensor includes a sensor housing positionable in the downhole tool, a sensing solution positionable in the housing (the sensing solution including a mediator reactive to target chemicals), a gas permeable membrane to fluidly isolate the downhole fluid from the sensing solution (the gas permeable membrane permitting the passage of gas to the sensing solution), and a plurality of electrodes positioned about the housing a distance from the gas permeable membrane to measure reaction by the sensing solution whereby downhole parameters may be determined.

12 Claims, 8 Drawing Sheets

(56) References Cited

U.S. PATENT DOCUMENTS

| | | | |
|---|---|---|---|
| 2004/0045350 A1* | 3/2004 | Jones | E21B 43/38 |
| | | | 73/152.23 |
| 2004/0159149 A1 | 8/2004 | Williams et al. | |
| 2006/0243603 A1* | 11/2006 | Jiang | E21B 47/00 |
| | | | 205/775 |
| 2008/0257730 A1* | 10/2008 | Jiang | E21B 49/082 |
| | | | 204/412 |
| 2009/0014325 A1 | 1/2009 | Jones et al. | |
| 2009/0090176 A1 | 4/2009 | Toribio et al. | |
| 2012/0103837 A1* | 5/2012 | Wall | G01N 27/62 |
| | | | 205/793 |
| 2013/0062222 A1 | 3/2013 | Lafitte et al. | |

OTHER PUBLICATIONS

International search report and written opinion for the equivalent PCT patent application No. PCT/US2014/070233 dated Mar. 25, 2015.
Examination report issued in the related AU application 2014366262, dated Nov. 24, 2017 (3 pages).
Office action issued in the related EA application 201691249, dated Nov. 17, 2017 (5 pages).
International Preliminary Report on patentability issued in the related PCT Application PCT/US2014/070233 dated Jun. 21, 2016 (9 pages).

\* cited by examiner

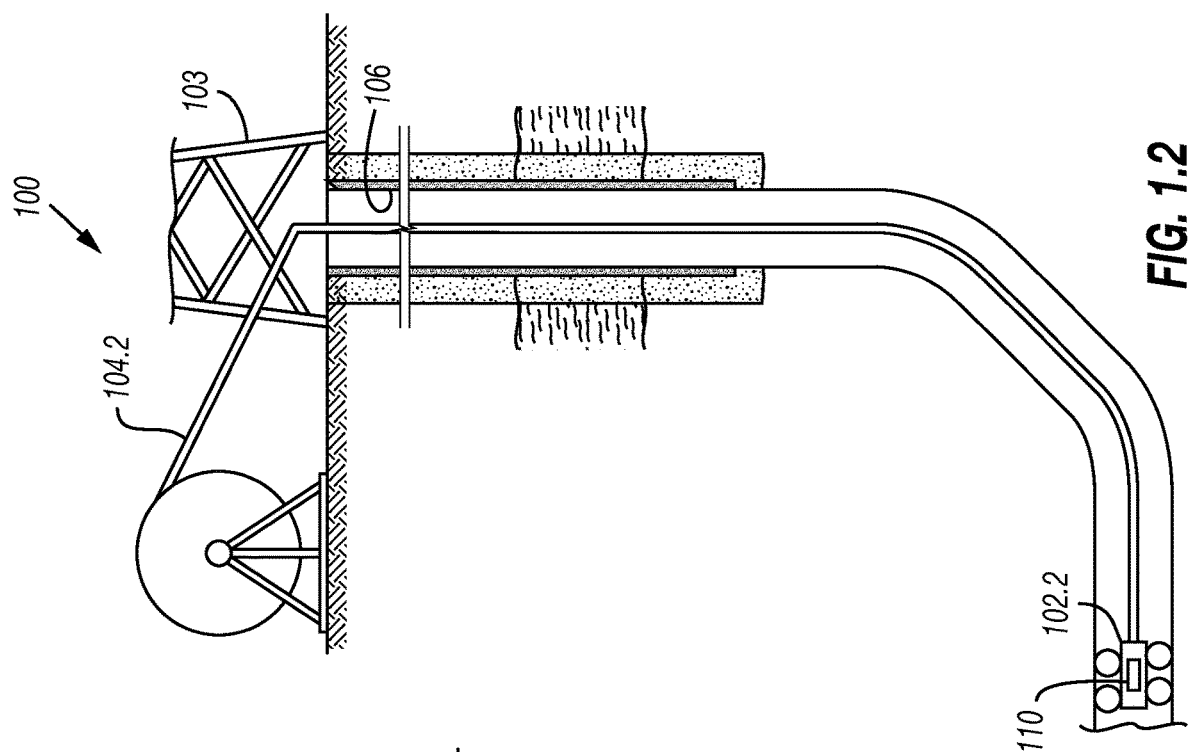
FIG. 1.2
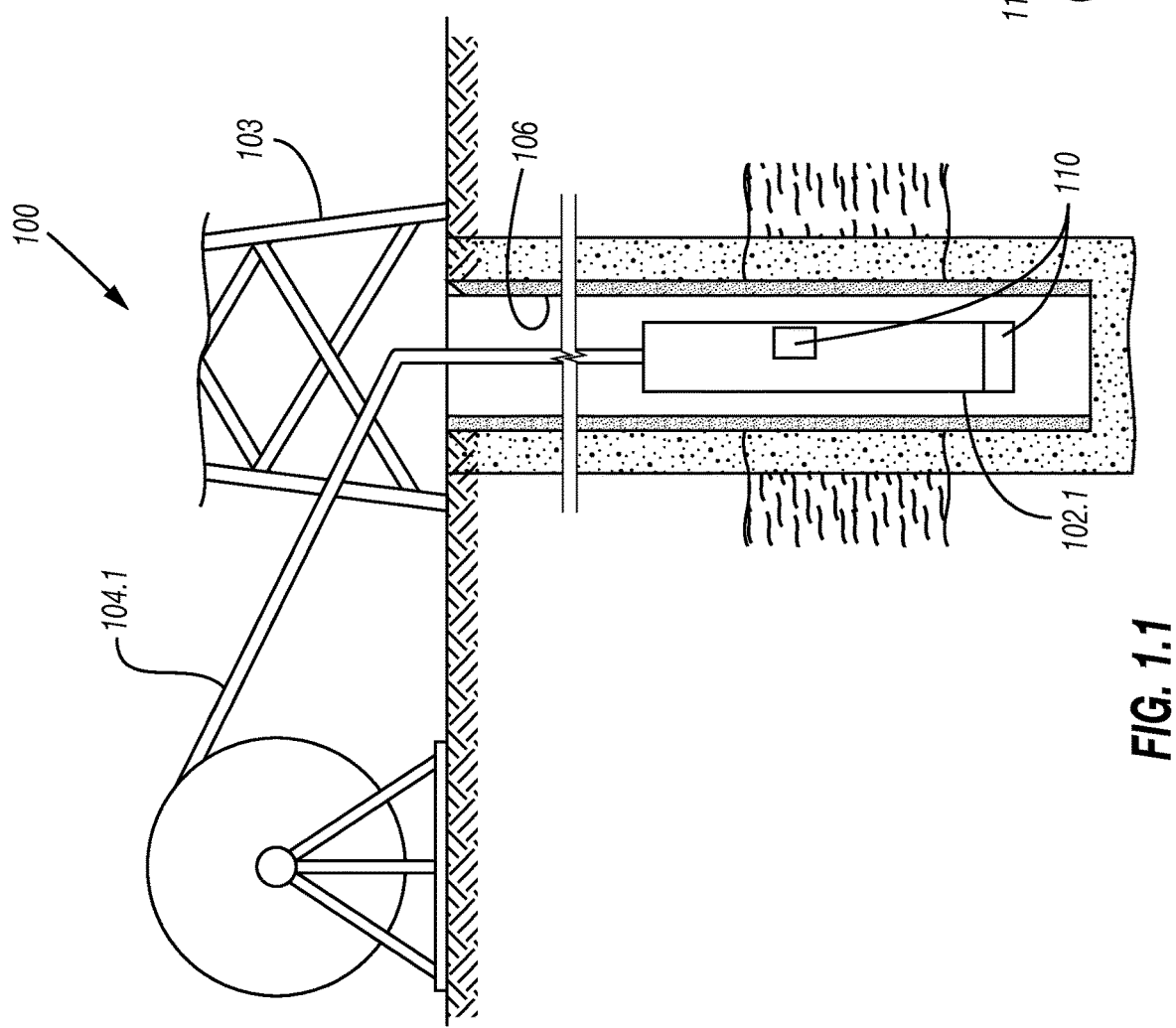
FIG. 1.1

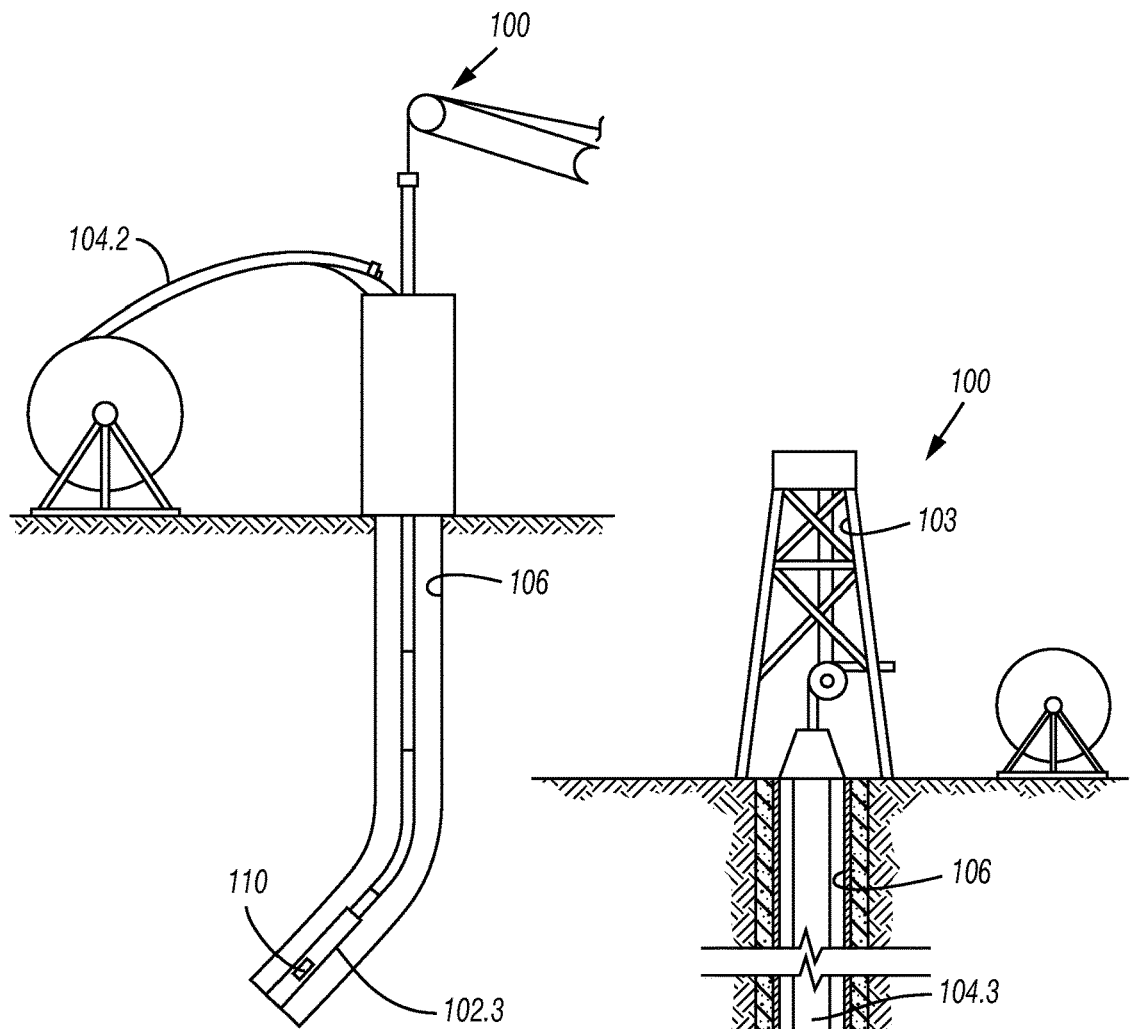
FIG. 1.3
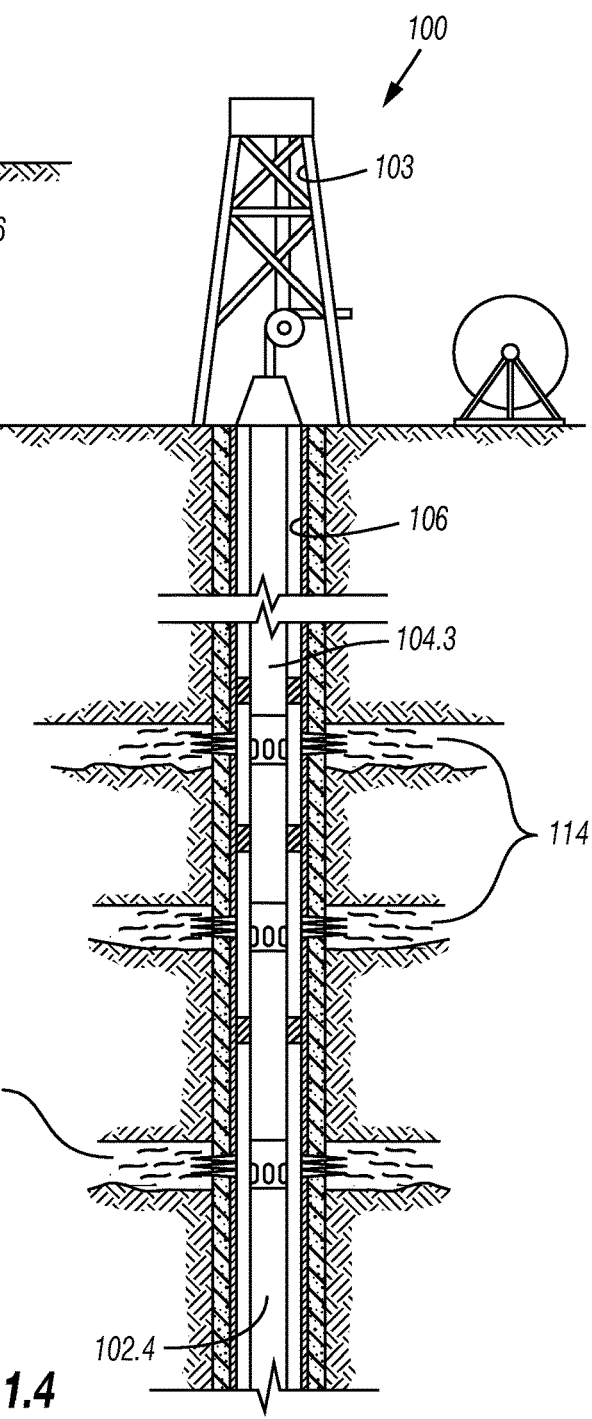
FIG. 1.4

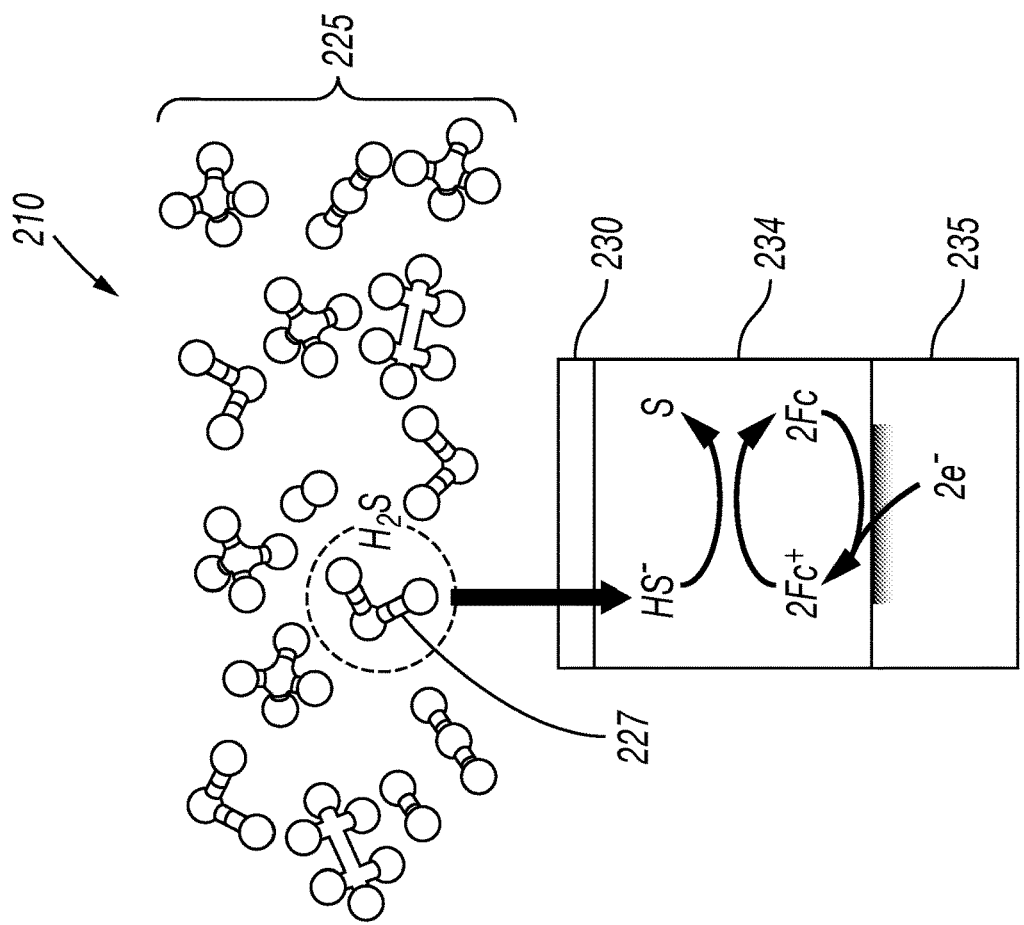
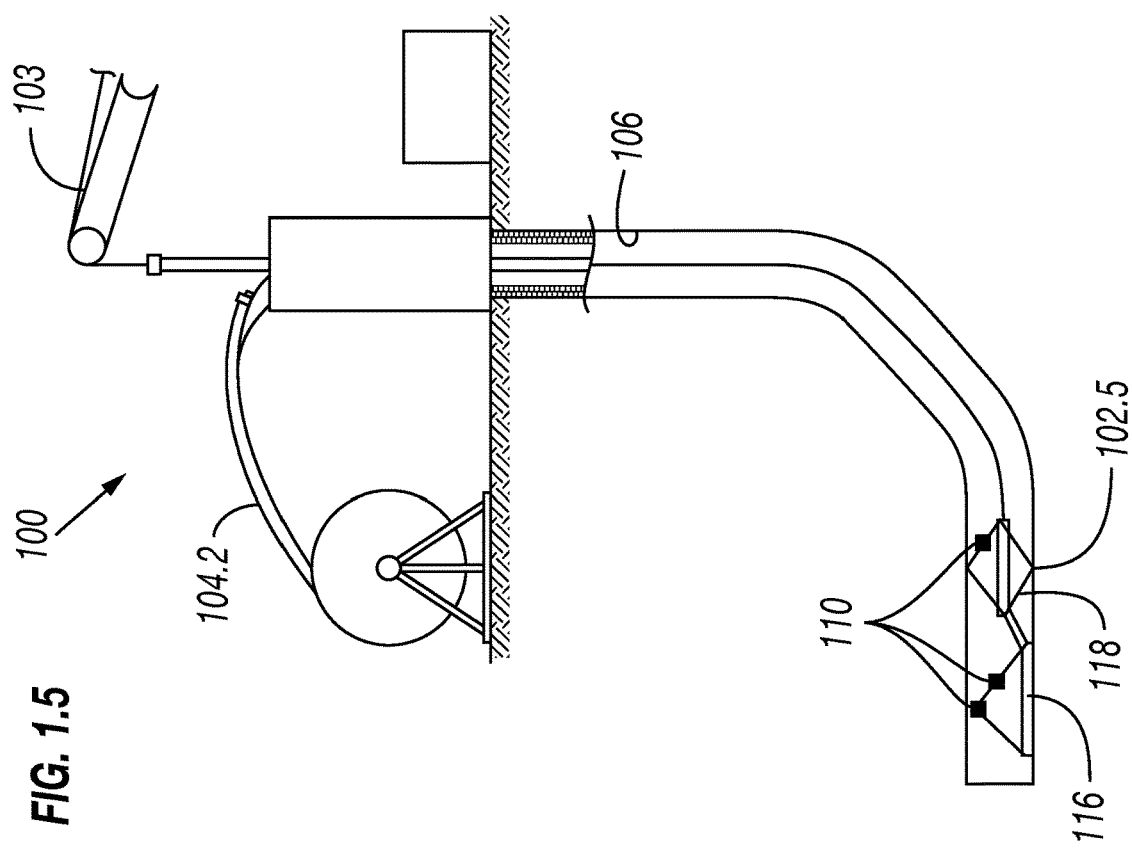
FIG. 1.5
FIG. 2

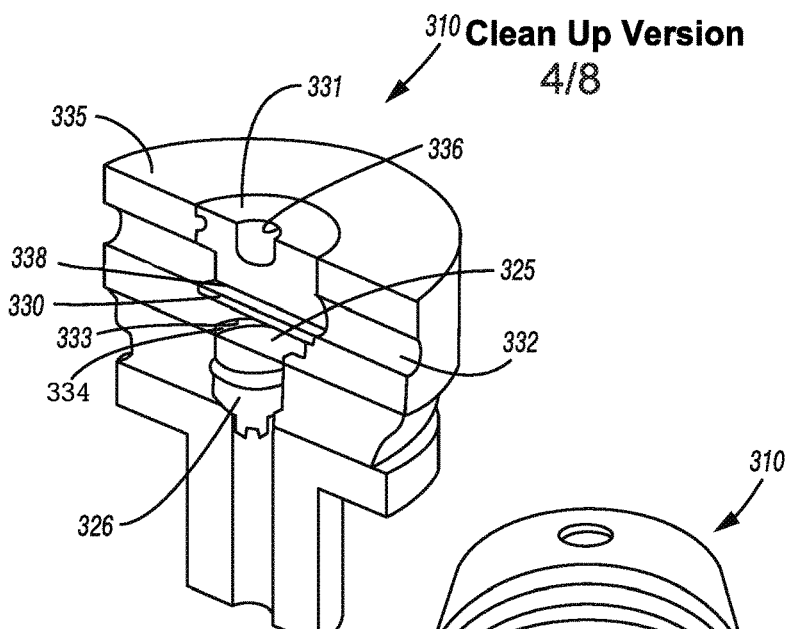
FIG. 3.1
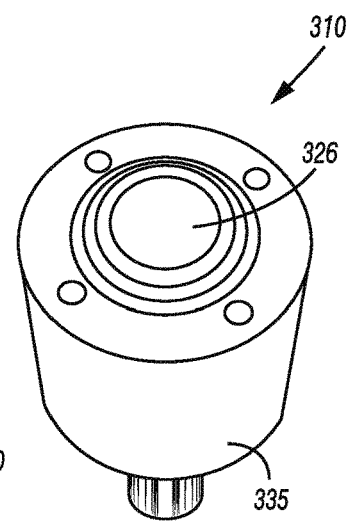
FIG. 3.2
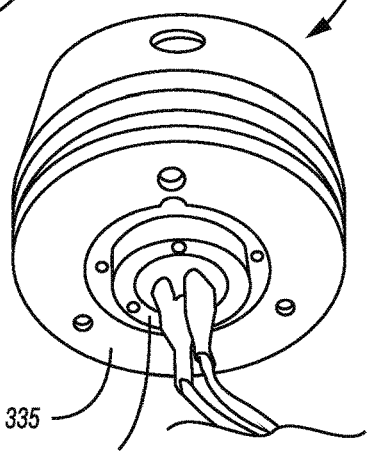
FIG. 3.3
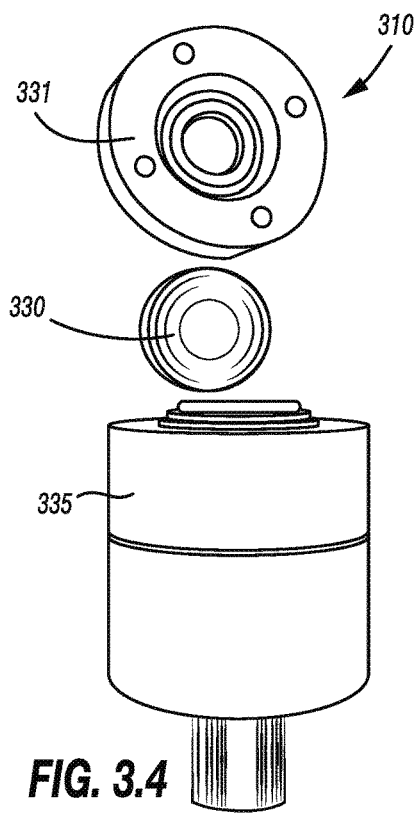
FIG. 3.4
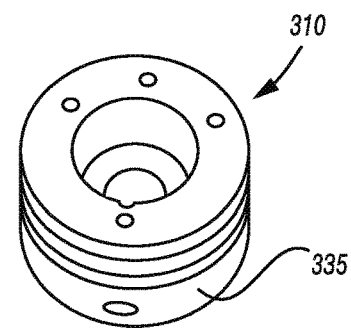
FIG. 3.5
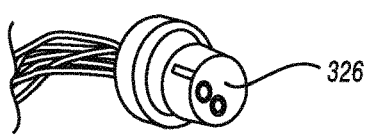

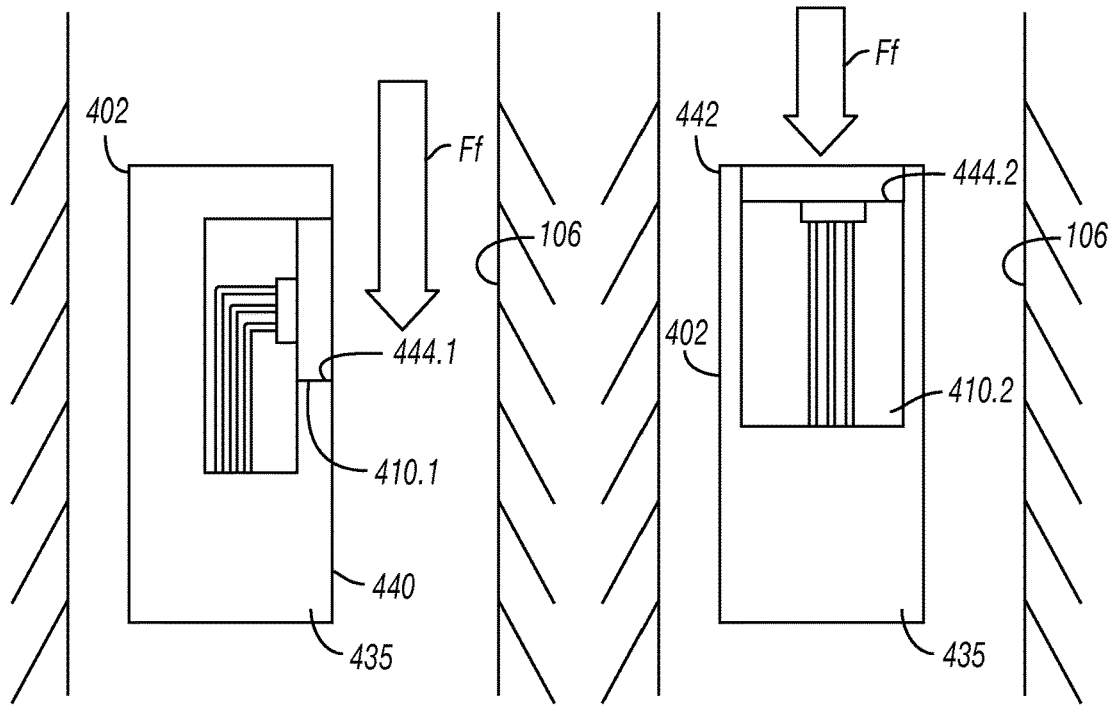
FIG. 4.1   FIG. 4.2
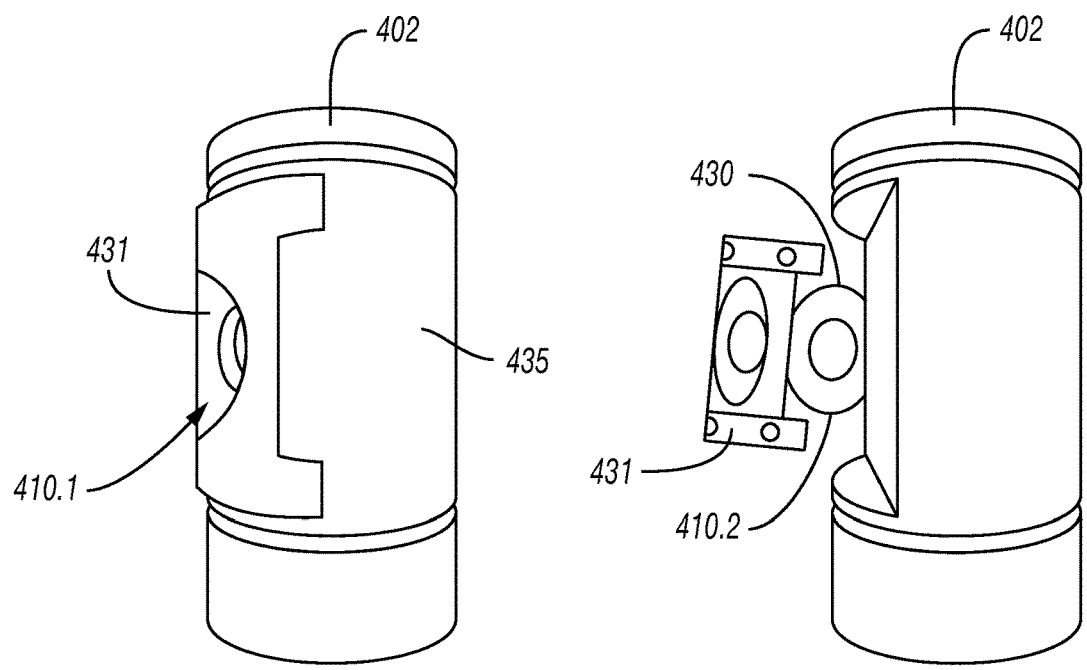
FIG. 4.3   FIG. 4.4

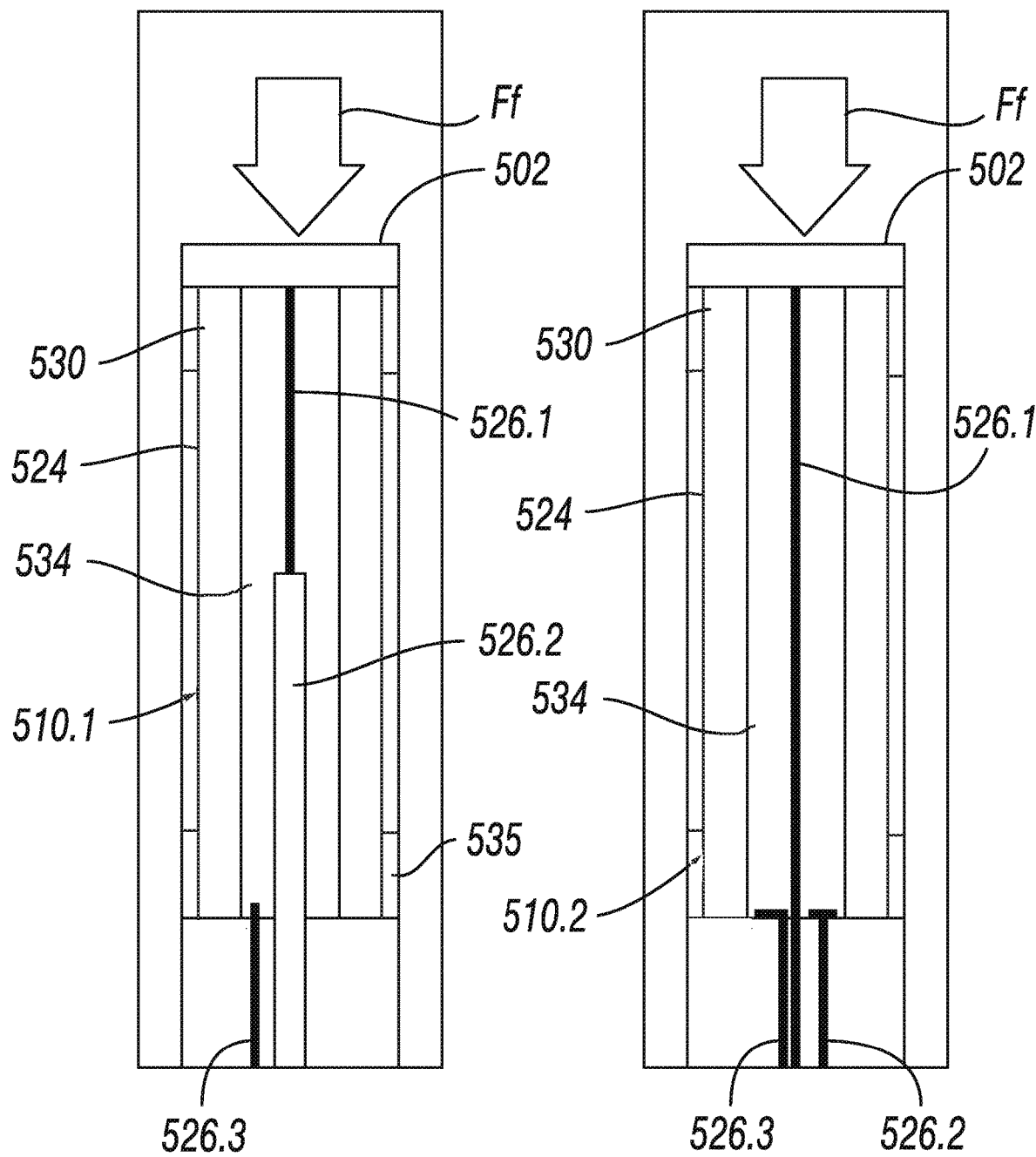

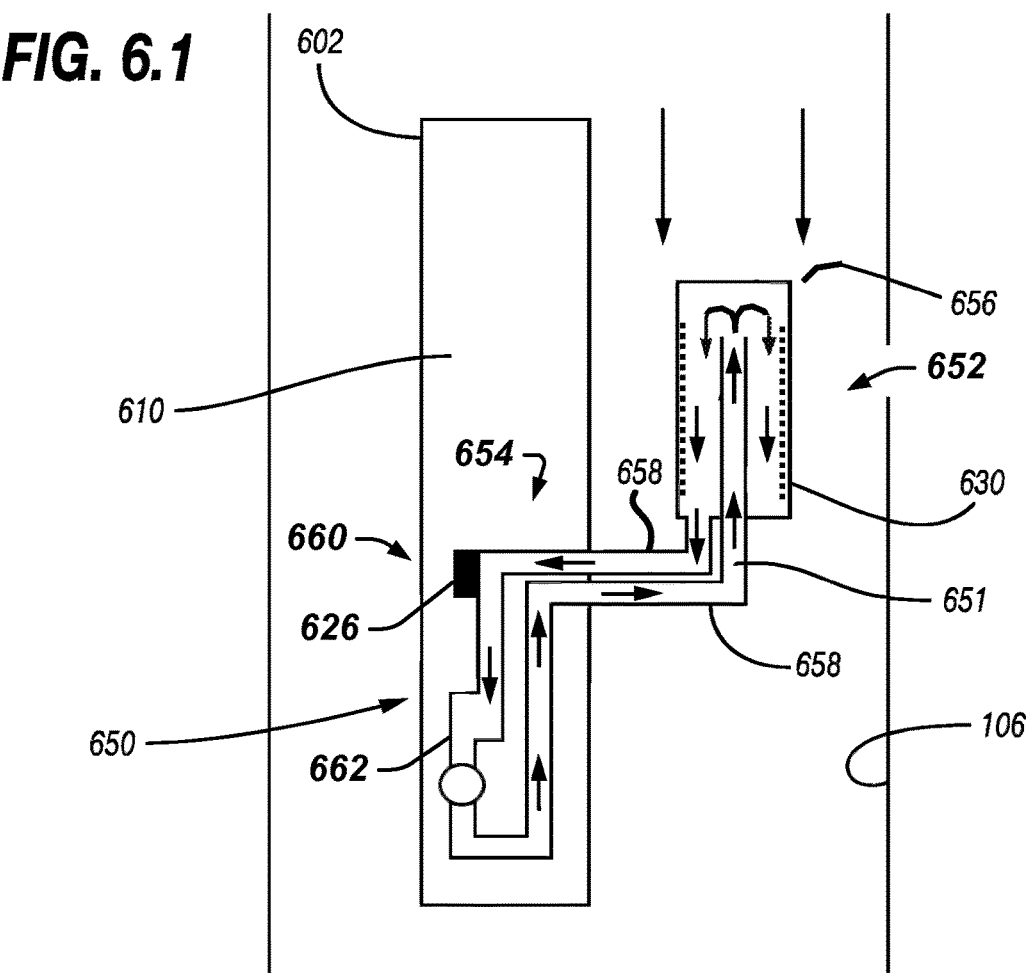
FIG. 6.1
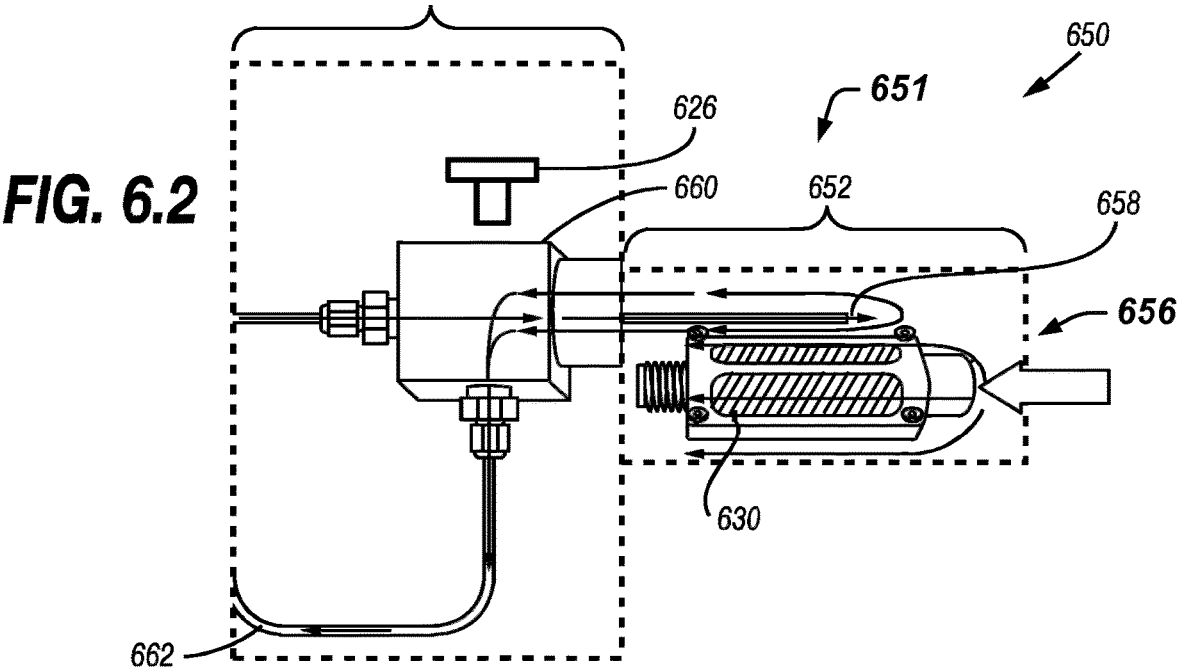
FIG. 6.2

DOWNHOLE ELECTROCHEMICAL FLUID SENSOR AND METHOD OF USING SAME

BACKGROUND

The present disclosure relates generally to wellsite operations. In particular, the present disclosure relates to determining downhole evaluation using, for example, sensors for measuring downhole parameters (e.g., fluid parameters).

Wellbores are drilled to locate and produce hydrocarbons. A downhole drilling tool with a bit at an end thereof is advanced into the ground to form a wellbore. As the drilling tool is advanced, drilling mud is pumped through the drilling tool and out of the drill bit to cool the drilling tool and carry away cuttings. The fluid exits the drill bit and flows back up to the surface for recirculation through the drilling tool. The drilling mud is also used to form a mudcake to line the wellbore.

During a drilling operation and later in the life of the well, various downhole evaluations may be performed to determine characteristics of the wellbore and surrounding formations. In some cases, the drilling tool may be provided with devices to test and/or sample the surrounding formation and/or fluid contained in reservoirs therein. In some cases, the drilling tool may be removed and a downhole wireline tool may be deployed into the wellbore to perform formation evaluation, such as testing and/or sampling. Samples or tests may be taken, for example, to determine whether valuable hydrocarbons are present.

Downhole tools may be provided with fluid analyzers, logging while drilling, measurement while drilling, and/or sensors to measure downhole parameters, such as fluid properties. Examples of downhole devices are provided in US Patent/Publication Nos. 2009/0014325, 2009/0090176, U.S. Pat. Nos. 6,223,822, 6,939,717, 7,222,671, 7,520,160, 7,025,138, 7,458,252, and 8,177,958, the entire contents of which are hereby incorporated by reference herein.

SUMMARY

In at least one aspect, the disclosure relates to an electrochemical fluid sensor for a downhole tool positionable in a wellbore penetrating a subterranean formation. The wellbore has a downhole fluid therein. The electrochemical fluid sensor includes a sensor housing positionable in the downhole tool, a sensing solution positionable in the housing (the sensing solution comprising a mediator reactive to target chemicals), a gas permeable membrane to fluidly isolate the downhole fluid from the sensing solution (the gas permeable membrane permitting the passage of gas to the sensing solution), and a plurality of electrodes positioned about the housing a distance from the gas permeable membrane to measure reaction by the sensing solution whereby downhole parameters may be determined.

In another aspect, the disclosure relates to a system for sensing downhole parameters of a downhole fluid in a wellbore penetrating a subterranean formation. The system includes a downhole tool deployable into the wellbore and an electrochemical fluid sensor. The electrochemical fluid sensor includes a sensor housing positionable in the downhole tool, a sensing solution positionable in the housing (the sensing solution comprising a mediator reactive to target chemicals), a gas permeable membrane to fluidly isolate the downhole fluid from the sensing solution (the gas permeable membrane permitting the passage of gas (free or dissolved) to the sensing solution), and a plurality of electrodes positioned about the housing a distance from the gas permeable membrane to measure reaction by the sensing solution whereby downhole parameters may be determined.

Finally, in another aspect, the disclosure relates to a method of sensing downhole parameters of a downhole fluid in a wellbore penetrating a subterranean formation. The method involves deploying a downhole tool into the wellbore. The downhole tool has at least one electrochemical fluid sensor thereabout. The electrochemical fluid sensor includes a sensor housing, a sensing solution comprising a mediator reactive to target chemicals, a gas permeable membrane, and a plurality of electrodes. The method also involves exposing the sensing solution to gas in the downhole fluid by isolating the sensing solution from the downhole fluid with the gas permeable membrane and measuring reactions of the sensing solution with the plurality of electrodes a distance from the gas permeable membrane.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Embodiments of the downhole electrochemical measurement apparatus, method and system are described with reference to the following figures. The same numbers are used throughout the figures to reference like features and components.

FIGS. 1.1-1.5 depict schematic views, partially in cross-section, of a wellsite having various downhole tools with fluid sensors to measure downhole parameters in accordance with embodiments of the present disclosure;

FIG. 2 depicts a schematic view, partially in cross-section, of an electrochemical fluid sensor in accordance with embodiments of the present disclosure;

FIGS. 3.1-3.5 are various views of a fluid sensor in accordance with embodiments of the present disclosure;

FIGS. 4.1-4.4 are schematic views of downhole tool with a fluid sensor in various positions relative to fluid flow in accordance with embodiments of the present disclosure;

FIGS. 5.1-5.2 are schematic cross-sectional views of a downhole tool with a fluid sensor having various membrane configurations in accordance with embodiments of the present disclosure;

FIGS. 6.1 and 6.2 are schematic diagrams depicting various views of a downhole tool with a sensor assembly in accordance with embodiments of the present disclosure.

DETAILED DESCRIPTION

Figure 7:
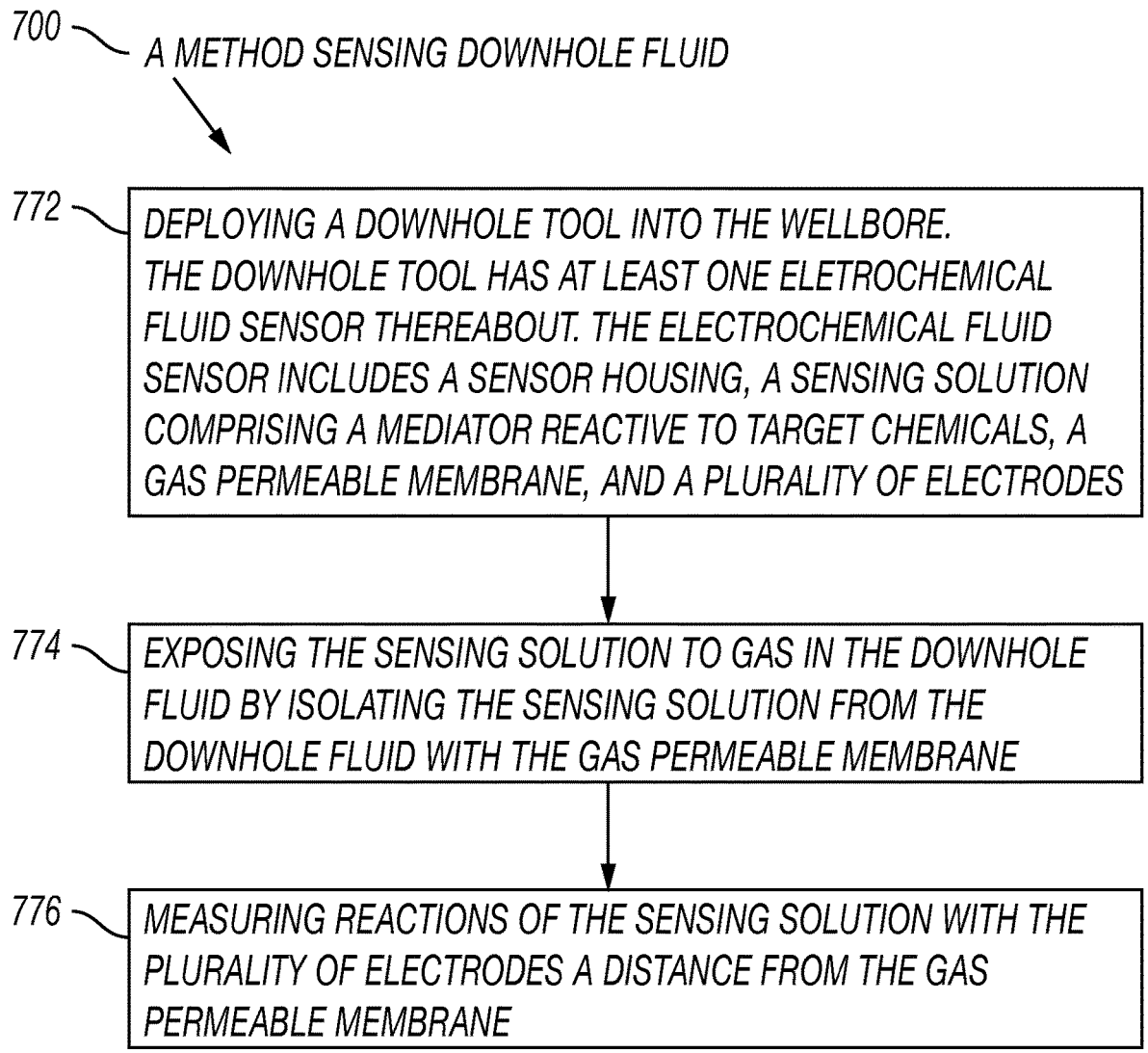
FIG. 7 is a method flow chart depicting a method of sensing downhole fluid parameters in accordance with embodiments of the present disclosure.

The description that follows includes apparatuses, methods, techniques, and instruction sequences that embody techniques of the inventive subject matter. However, it is understood that the described embodiments may be practiced without these specific details.

The present disclosure relates generally to wellsite operations and, in particular, to downhole sensors for measuring parameters of a downhole fluid during production operations. Measurements of fluid parameters may be taken using an electrochemical fluid sensor deployed into a wellbore on a downhole tool. The electrochemical fluid sensor may include a protective membrane with a combination of cell sensors and cell electrodes to measure various fluid parameters, and a sensing solution. The cell sensors may include an analyte sensor, a temperature sensor, a pH sensor, and/or other cell sensors. The sensing solution may be reactive to certain analytes in the downhole fluid to generate electrical signals measurable by the cell sensors whereby parameters of chemicals in the downhole fluid may be measured.

The downhole sensor may be an electrochemical fluid sensor for measuring fluid components within a produced fluid, such as, for example, $CO_2$, $CH_4$, $C_2H_6$, $H_2S$, and/or other downhole fluids. Fluid parameters measured by the electrochemical fluid sensor may be used, for example, to assist in deciding which, if any, production zones should be isolated, what materials should be used for pipelines, to provide information about how much scavenger can be injected, and/or for other purposes. The electrochemical fluid sensor may also be used to take various measurements to determine phase behavior, chemical composition, and/or downhole gases (e.g., hydrogen sulfide ($H_2S$), carbon dioxide ($CO_2$), methane ($CH_4$), etc.) Outputs from the electrochemical fluid sensor may be combined, using a measurement chain, to determine various downhole parameters, such as pressure and/or concentration of $H_2S$ in downhole fluids.

Downhole fluids may be measured and/or analyzed to determine phase behavior and chemical composition. Chemical composition of downhole fluids and/or concentrations of downhole gases may be used, for example, to evaluate producibility and/or economic value of hydrocarbon reserves. Certain chemicals, such as $H_2S$ and $CO_2$, may affect downhole operations. For example, the presence of certain chemicals, such as $CO_2$ and $H_2S$, may lead to failures due to, for example, corrosion, stress cracking, welding, pitting, erosion, galvanic, and stress deterioration. $H_2S$ may be detected in fluids found in the permeable formations of oil wells. Sulfur content of crude oils may be in the range of from about 0.30 to about 0.80 weight percent. The content of $H_2S$ in natural gas may be in the range of from about 0.01 to about 0.40 weight percent, and concentrations of $H_2S$ in natural gas of up to 30 weight percent.

FIGS. 1.1-1.5 depict examples of environments in which subject matter of the present disclosure may be implemented. Each figure depicts a wellsite 100 with a wellbore 106 having a downhole tool 102.1-102.5 deployed into the wellbore 106 from a rig 103 to perform wellbore operations. Each of the downhole tools 102.1-102.5 having one or more fluid sensors 110 thereon for measuring downhole fluid and/or other parameters.

FIG. 1.1 depicts a downhole tool 102.1 deployed on a wireline 104.1 in the wellbore 106. FIG. 1.2 depicts a downhole tractor 102.2 deployed on a wire 104.2 in the wellbore 106. The tractor tool 102.2 may be controlled through the wire 104.2 for advancing and withdrawing the tool 102.2 about the wellbore 106. FIG. 1.3 depicts a downhole injection tool 102.3 deployed on a coiled tubing 104.2 in the wellbore 106.

FIGS. 1.4 and 1.5 depict a downhole tool 102.4 deployed on a production tubing 104.3 in the wellbore 106. The production tool 102.4 may be used, for example, for logging hydrocarbon production from different production zones 114 along the wellbore 106. FIG. 1.5 depicts a downhole logging tool 102.5 deployed on a coiled tubing 104.2 in the wellbore 106. The logging tool 102.5 may have a body 116 with extendable arms 118 for positioning the fluid sensors 110 about the wellbore 106 for measuring about different locations about the wellbore 106.

The fluid sensor 110 may be positioned about one or more downhole tools, such as the downhole tools 102.1-105, to take various measurements about the wellbore 106. The measurements may be, for example, measurements of downhole fluid composition.

The fluid sensors 110 may be electrochemical sensors reactive to certain target chemicals 227, such as H2S and/or other corrosive and/or potentially detrimental materials, in the downhole fluid 225 as schematically shown in FIG. 2. As also schematically shown, the fluid sensor 110 may have a membrane 230 engageable with the downhole fluid 225, and a sensing solution 234 with a mediator reactive to the target chemicals. The fluid sensor 110 also has an electrode 235 to to measure electrochemical reaction of the target chemicals by the sensing solution 234.

The fluid sensor 110 may have different configurations and/or shapes (e.g., cylindrical, planar, conical, spherical, or some combination thereof). FIGS. 3.1-3.5 show an example form of an electrochemical fluid sensor 310 which may be used as the fluid sensor 110 and/or 210. FIG. 3.1 shows a cross-sectional view of the fluid sensor 310. FIG. 3.2 shows a top perspective view of the fluid sensor 310. FIG. 3.3 shows a bottom perspective view of the fluid sensor 310. FIG. 3.4 shows an exploded view of the fluid sensor 310. FIG. 3.5 shows another exploded view of a portion of the fluid sensor 310.

The fluid sensor 310 includes a housing 335 in which electrodes 326 are mounted against a bulkhead 328. A gas permeable membrane 330 is mounted between the electrodes 326 and fluid flowing past the sensor 310. The housing 335 may be a bulkhead formed of a nonmagnetic material, such as polyether ether ketone (PEEK). The housing 335 has a flowline 332 therethrough for receiving downhole fluid. A coverplate 331 may be provided at an exterior inlet of the housing 335. The housing 335 also has a chamber 333 charged with a sensing solution 334 and receiving the electrode 326. The housing may also have a retaining ring 337 to secure the membrane 330 in the housing 335.

The sensing solution 334 may include, for example, an electrocatalytic mediator solution (e.g., water-soluble ferrocene) dissolved in an aqueous solution. This type of mediator may oxidize at a sensing surface 325 of the electrode 326 to react with the target chemical 227 (FIG. 2). The oxidation may form ions which, when a gas such as $H_2S$ is present, are reduced back to their parent state. The mediator may then be re-oxidized at the sensing surface 325. The sensing surface 325 may be configured to measure electrical changes resulting from the reactions generated by oxidation of the sensing solution 334.

The gas permeable membrane 330 may be mounted in the housing 335 in a position to be exposed to the downhole fluid flowing past the sensor 210. The position may be selected so that fluid can be transported through the membrane 330 and into contact with the sensing solution 334. The cover plate 331 is mounted in the housing 335 for holding the membrane 330 in place. The cover plate 331 has an opening 336 for allowing fluid flowing through the flowline to contact the membrane 330. A filter 338 formed of a protective material, such as gauze or a fine mesh, may be mounted in the cover plate 331 to protect the membrane 330 from particles in the flowing fluid.

The fluid sensor 310 may be compact in design with a small distance between the membrane 330 and the electrochemical sensing surface 325 of the electrodes 326. For example, the membrane 330 may be spaced from the sensing surface 325 at a minimum distance of, for example, about 100 microns to ensure that a diffusion controlled response is obtained and that the membrane 330 is not impinging on a diffusion layer of the electrodes 326. The distance between the membrane 330 and the electrodes 326 may influence the response time of the sensor 310.

Referring to FIGS. 2 and 3.1, the sensor 310 may operates by providing, for example, a mechanistic pathway detailing the electrocatalytic reduction of ferrocenium by sulfide. For example, ferrocene may oxidize at the sensing surface 325 of the electrochemical sensor 310 to form ferricenium ions when sulfide is present, and to homogeneously reduce the ferricenium ion back to ferrocene which can be re-oxidized at the sensing surface as shown, for example, in FIG. 2. An apparent increase in ferricenium ions may perturb a baseline voltammetry through an increase in oxidative current (and charge), which can be measured by the electrochemical sensor 310 and used to determine the concentration of chemicals (e.g., $H_2S$) in the downhole fluid.

As shown in FIGS. 4.1-4.4, the fluid sensor may be placed about a downhole tool in different positions for measuring fluid parameters. FIGS. 4.1-4.4 show a fluid sensor 410.1, 410.2 (which may be any fluid sensor described herein) positioned about a downhole tool 402 (which may be any downhole tool described herein). FIG. 4.1 shows a cross-sectional view of the fluid sensor 410.1 along an outer side surface 440 of the downhole tool 402 in a position parallel to fluid flow Ff1 as depicted by the arrow. FIG. 4.2 shows a cross-sectional view of the fluid sensor 410.2 along an outer end 442 surface of the downhole tool 402 in a position perpendicular to fluid flow Ff as depicted by the arrow. FIG. 4.3 shows a perspective view of the downhole tool of FIG. 4.1. FIG. 4.3 shows an exploded view of the downhole tool of FIG. 4.3.

The fluid sensor 410.1, 410.2 may be positioned in a recess 444.1, 444.2 within the downhole tool 402 for protection and/or to prevent obstruction to fluid flow. As shown, the downhole tool 402 has a housing 435 with a cover plate 431 over the membrane 430 depressed within recess 444.1, 444.2.

FIGS. 5.1 and 5.2 show schematic views of a downhole tool 502 with cylindrical configurations of a fluid sensor 510.1, 510.2. In these figures, the fluid sensor 510.1, 510.2 has a cylindrical membrane 530 positioned in housing 535. This cylindrical configuration may be used to increase surface area of a sensing surface 524 of the fluid sensor. The response time may be determined by a ratio of the surface area of the cylindrical membrane 530 to the volume of sensing solution 534. The cylindrical membrane 530 may allow for a minimal distance between the membrane 530 and electrodes 526.1-526.3.

In FIG. 5.1, the working electrode 526.1 and counter electrode 526.2 are mounted in the sensor 510.1 inside the cylindrical membrane 530, and reference electrode 526.3 is outside the cylindrical membrane 530. The working electrode 526.1 extends the length of the membrane 530 and the counter electrode 526.2 extends partially along the cylindrical membrane 530. The configuration of FIG. 5.2 is the same, except that both the counter and reference electrodes 526.2, 526.3 are outside the cylindrical membrane 530.

FIGS. 6.1 and 6.2 depict a sensor assembly 650 for circulating downhole fluid about a fluid sensor 660. The sensor 660 may be any of the fluid sensors described herein. The sensor assembly 650 includes a fluid (or wet) portion 652 and a sensing (or dry) portion 654. The fluid portion 652 includes an inlet 656 to receive downhole fluid, a cylindrical membrane 630 permeable to gas from the downhole fluid such that gas from the downhole fluid may pass through the membrane but the downhole fluid itself may not, thereby keeping the downhole fluid fluidly isolated from sensing fluid within a fluid flowline 658 to pass the sensing fluid and gas passing through the membrane 630 from the downhole fluid to the sensing portion 654. The sensing portion 654 has a sensor 660 with electrodes 626 and a mediator flowline 662 to circulate the sensing fluid past the sensor 660.

The fluid sensor 660 may be exposed on one side to the fluid in the fluid flowline 658 and on another side to the sensing fluid in the mediator flowline 662 for interaction therebetween. A gas permeable membrane 630 may be positioned in the fluid inlet 656. Fluid may be passed into the inlet 656 and gas from the fluid may pass through the gas permeable membrane 630 to mix with the sensing fluid in the fluid flowline 658 for sensing by the electrodes 626.

FIG. 6.1 shows the downhole tool 602 with the sensor assembly 650. The sensor assembly 650 is in the downhole tool 602 with the cylindrical gas permeable membrane 630 positioned in an arm 651 extendable from the downhole tool 602. FIG. 6.2 shows a detailed view of the sensor assembly 650. In FIG. 6.2, as shown by the horizontal arrows along the exterior length of the housing, the downhole fluid is fluidly isolated from the fluid flowline 658 which, when assembled, is located interior to the cylindrical gas permeable membrane 630 (shown via cross-hatch) within the housing. These figures demonstrate an extended configuration with the membrane 630 positionable a distance from the electrodes 626. The electrodes 626 may be a distance of about 100 microns from the membrane 630.

The sensing solution may be circulated in the mediator flowline 662 and through the fluid flowline 658, which is positioned within the membrane 630, such that a gas from the downhole fluid may pass through the membrane 630 into the sensing solution in the fluid flowline 658 and to the electrodes 626. A flow velocity of the sensing solution may be used to interact with the sensor electrodes 626. Flow may be stopped and/or calibrated during measurement. Because mediator flow velocity has an effect on the behavior of the electrodes 626, the electrodes 626 can either be calibrated for the flow velocity or the flow can be temporarily stopped while measurements are taken.

FIG. 7 is a flow chart depicting a method 700 of sensing fluid parameters. The method 700 may be performed using any combination of fluid sensors and/or sensing assemblies described herein. The method involves 772 deploying a downhole tool into the wellbore, the downhole tool having at least one electrochemical fluid sensor thereabout. The electrochemical fluid sensor includes a sensor housing, a sensing solution comprising a mediator reactive to target chemicals, a gas permeable membrane, and a plurality of electrodes. The method also involves 774 exposing the sensing solution to gas in the downhole fluid by isolating the sensing solution from the downhole fluid with the gas permeable membrane, and 776 measuring reactions of the sensing solution with the plurality of electrodes a distance from the gas permeable membrane.

The method may also involve circulating the downhole fluid past a first side of the gas permeable membrane and circulating the sensing solution about a second side of the gas permeable membrane. The method may be performed in any order, and/or repeated as desired.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. An electrochemical fluid sensor for a downhole tool positionable in a wellbore penetrating a subterranean formation, the wellbore having a downhole fluid therein, the electrochemical fluid sensor comprising:
    a sensing portion positionable in the downhole tool, the sensing portion comprising:
        a sensor body;
        a plurality of electrodes positioned within the sensor body; and
        part of a mediator flowline to circulate a sensing solution about the plurality of electrodes, the sensing solution comprising a mediator reactive to target chemicals; and
    a fluid portion positionable outside the downhole tool and connected to the sensing portion, the fluid portion comprising:
        part of the mediator flowline; and
        a gas permeable membrane to fluidly isolate the downhole fluid from the sensing solution, the gas permeable membrane permitting a passage of gas to the sensing solution; and
    wherein the plurality of electrodes measures a change in an electrical current based on electrochemical reaction by the sensing solution whereby concentration of the target chemicals may be determined based on the measured change.

2. The electrochemical fluid sensor of claim 1, wherein the plurality of electrodes comprises at least one of a working electrode, a counter electrode, or a reference electrode.

3. The electrochemical fluid sensor of claim 1, wherein the mediator comprises an electrocatalytic mediator.

4. The electrochemical fluid sensor of claim 3, wherein the mediator comprises ferrocene.

5. A system for sensing downhole parameters of a downhole fluid in a wellbore penetrating a subterranean formation, the system comprising:
    a downhole tool deployable into the wellbore; and
    an electrochemical fluid sensor comprising:
        a sensing portion in the downhole tool, comprising:
            a sensor body;
            a plurality of electrodes positioned within the sensor body; and
            part of a mediator flowline to circulate a sensing solution about the plurality of electrodes, the sensing solution comprising a mediator reactive to target chemicals; and
        a fluid portion positionable outside the downhole tool and connected to the sensing portion, the fluid portion comprising:
            part of the mediator flowline; and
            a gas permeable membrane positioned in the housing to fluidly isolate the downhole fluid from the sensing solution, the gas permeable membrane permitting a passage of gas to the sensing solution; and
    wherein the plurality of electrodes measures a change in an electrical current based on electrochemical reaction by the sensing solution whereby concentration of the downhole parameters of the target chemicals may be determined based on the measured change.

6. The system of claim 5, wherein the downhole tool is one of a wireline tool, a production tool, a coiled tubing tool, a logging tool, or a combination thereof.

7. The system of claim 5, wherein the downhole tool has a recess to receive the electrochemical fluid sensor therein.

8. The system of claim 7, wherein the recess is positioned about an outer side surface of the downhole tool.

9. The system of claim 7, wherein the recess is positioned about a top side surface of the downhole tool.

10. The system of claim 5, wherein the downhole tool has an arm extendable therefrom and wherein at least the fluid portion of the electrochemical fluid sensor is positionable in the arm.

11. The system of claim 5, wherein the electrochemical fluid sensor is positionable in the downhole tool perpendicular to fluid flow.

12. The system of claim 5, wherein the electrochemical fluid sensor is positionable in the downhole tool parallel to fluid flow.

* * * * *